(12) United States Patent
Ahmad et al.

(10) Patent No.: US 10,280,124 B2
(45) Date of Patent: *May 7, 2019

(54) METHODS FOR MAKING ACTIVE CRYSTALLINE MATERIALS

(71) Applicant: CPI INNOVATION SERVICES LIMITED, Teesside (GB)

(72) Inventors: Ruksanna Ahmad, Redcar Cleveland (GB); Jeremy Cooper, Redcar Cleveland (GB); Isaac Odiase, Merseyside (GB)

(73) Assignee: CPI Innovation Services Limited, Redcar (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/233,089

(22) Filed: Aug. 10, 2016

(65) Prior Publication Data

US 2016/0347680 A1 Dec. 1, 2016

Related U.S. Application Data

(63) Continuation of application No. 14/651,404, filed as application No. PCT/GB2013/053255 on Dec. 11, 2013, now Pat. No. 9,439,914.

(30) Foreign Application Priority Data

Dec. 11, 2012 (GB) .................................. 1222287.3

(51) Int. Cl.
| | | |
|---|---|---|
| *C07B 63/00* | (2006.01) | |
| *A61K 31/60* | (2006.01) | |
| *A61K 31/522* | (2006.01) | |
| *A61K 31/194* | (2006.01) | |
| *A61K 31/455* | (2006.01) | |
| *A61K 31/55* | (2006.01) | |
| *A61K 31/505* | (2006.01) | |
| *C07C 51/43* | (2006.01) | |
| *C07D 213/82* | (2006.01) | |
| *C07D 223/26* | (2006.01) | |
| *C07D 239/42* | (2006.01) | |
| *C07D 473/12* | (2006.01) | |

(52) U.S. Cl.
CPC ............ *C07B 63/00* (2013.01); *A61K 31/194* (2013.01); *A61K 31/455* (2013.01); *A61K 31/505* (2013.01); *A61K 31/522* (2013.01); *A61K 31/55* (2013.01); *A61K 31/60* (2013.01); *C07C 51/43* (2013.01); *C07D 213/82* (2013.01); *C07D 223/26* (2013.01); *C07D 239/42* (2013.01); *C07D 473/12* (2013.01); *C07B 2200/13* (2013.01)

(58) Field of Classification Search
CPC ...................................................... C07B 63/00
See application file for complete search history.

(56) References Cited

U.S. PATENT DOCUMENTS

| | | | |
|---|---|---|---|
| 7,927,613 | B2 | 4/2011 | Almarsson et al. |
| 8,318,943 | B1 | 11/2012 | Sun et al. |
| 9,439,914 | B2 * | 9/2016 | Ahmad ................... C07B 63/00 |
| 2005/0181041 | A1 | 8/2005 | Goldman |
| 2007/0287184 | A1 | 12/2007 | Telkki et al. |
| 2009/0054455 | A1 | 2/2009 | Devarakonda et al. |
| 2010/0204204 | A1 | 8/2010 | Zaworotko et al. |
| 2013/0102797 | A1 | 4/2013 | Tu et al. |

FOREIGN PATENT DOCUMENTS

| | | |
|---|---|---|
| EP | 1715008 A2 | 10/2006 |
| EP | 2170284 A2 | 4/2010 |
| EP | 2177215 A1 | 4/2010 |
| EP | 2199274 A1 | 6/2010 |
| EP | 2361247 A2 | 8/2011 |
| WO | WO 1999/12623 A1 | 3/1999 |
| WO | WO 2008/143500 A1 | 11/2008 |
| WO | WO-2011097372 A2 | 8/2011 |
| WO | WO 2014/091226 A1 | 6/2014 |
| WO | WO 2014091226 A1 * 6/2014 ............. C07B 63/00 |

OTHER PUBLICATIONS

International Search Report and Written Opinion for GB 1222287.3 dated Oct. 8, 2013.
International Search Report and Written Opinion for PCT/GB2013/053255 dated Mar. 20, 2014.
Aitipamula, S., et al., "Polymorphs, Salts, and Cocrystals: What's in a Name?," Crystal Growth and Design, vol. 12, Apr. 12, 2012, pp. 2147-2152.
Childs, S., et al., "The Salt-Cocrystal Continuum: The Influence of Crystal Structure on Ionization State," Molecular Pharmaceutics, vol. 4, No. 3, 2007, pp. 323-338.
Delori, A., et al., "The role of mechanochemistry and supramolecular design in the development of pharmaceutical materials," CrystEngComm, 2012, vol. 14, pp. 2350-2362.

* cited by examiner

*Primary Examiner* — Matthew P Coughlin
(74) *Attorney, Agent, or Firm* — Winstead PC

(57) ABSTRACT

The present invention relates to an active crystalline material, especially an active multicomponent crystalline material such as a salt or a cocrystal, which may be made by dispersing precursor components of the active crystalline material in a liquid medium which comprises an antisolvent, maintaining the dispersion for a period during which the active crystalline material is formed, and, during said period, exposing the dispersion to a solvent, which solvent being present in the liquid medium in a minor proportion by weight thereof.

27 Claims, 3 Drawing Sheets

METHODS FOR MAKING ACTIVE CRYSTALLINE MATERIALS

CLAIM OF PRIORITY

The present application is a continuation application of U.S. application Ser. No. 14/651,404, filed on Jun. 11, 2015 and entitled "METHODS FOR MAKING ACTIVE CRYSTALLINE MATERIALS," which is a National Stage filing under 35 U.S.C. § 371 of International Patent Application No. PCT/GB2013/053255, filed on Dec. 11, 2013 and entitled "METHODS FOR MAKING ACTIVE CRYSTALLINE MATERIALS," which claims the benefit of and priority to United Kingdom Patent Application No. 1222287.3, filed on Dec. 11, 2012, which are incorporated by reference herein in their entireties.

FIELD OF THE INVENTION

The invention relates to methods for making active crystalline materials, which materials may be single crystal or polymorphic crystalline materials, or may be multicomponent crystals such as salts or cocrystals or combinations of salts and cocrystals. More particularly, the invention relates to methods for making active crystalline materials, which materials are multicomponent crystals. More especially, the invention relates to methods for making active crystalline materials, which materials are cocrystalline.

By "active material" is meant a material consisting of or comprising molecules that have an effect on a recipient organism of the material, whether the effect is beneficial, eg curing a medical condition, detrimental, eg controlling a plant pest, or relating to senses such as taste, touch etc. Commonly, an active material is a pharmaceutically active material; however, it is intended that other active materials, such as nutraceutical and agrochemical active materials, be encompassed within the scope of the term. An "active crystalline material" is an active material having a crystalline morphology. The terms "active" and "inactive" are used in this context in the specification.

BACKGROUND TO THE INVENTION

Active materials have been used throughout much of human history. In the modern era, significant use has been made of active materials extracted from natural sources or synthesised, whether to replace the natural source of the material or to generate new active analogues thereof or to generate new active materials. Such active materials may comprise a variety of morphologies including amorphous, crystalline, including single crystal, polymorphic, ionic crystalline and cocrystal morphologies. As is well understood in the art, there are many ways of manufacturing active materials including precipitation from solution, crystallisation from melts or solutions etc, although the preparation of cocrystalline materials may not be necessarily straight forward as is described in greater detail below.

The physiochemical properties of different morphological forms of the same active material may have a significant effect on inter alia the processability, deliverability and effectiveness of the active materials. A consequence of this is that the identification of different morphological forms of active materials with their corresponding physiochemical properties and effectiveness as an active material places a significant cost burden on researchers and developers of such materials, especially, but not solely, in the pharmaceutical industries. This, in turn, creates significant pressure to obtain intellectual property protection for active materials to ensure the costs of research and development may be recovered over the period of such protection. The inability to obtain intellectual property protection for new active materials may result in such materials not being developed at all.

The lapse of intellectual property protection for existing morphological versions of active materials or the potential lack of such protection for new active materials or for new morphological versions of known active materials, whether owing to the similarity to earlier versions of such active materials or for other reasons, has recently led to a significant interest in the development of cocrystalline active materials, which, owing to the novel molecular combinations and different physiochemical properties exhibited as compared to the corresponding free form of the active material, may be capable of being protected by intellectual property rights.

Cocrystals per se have been known and studied for many years. It is generally understood that cocrystals exhibit long-range order and the components thereof interact via intermolecular interactions including non-covalent interactions such as hydrogen and/or halogen bonding, $\pi$ interactions, ionic interactions, and van der Waals interactions. These intermolecular interactions, and the resulting crystal structures, generate physical and/or chemical properties, for example melting point, solubility, chemical stability, and mechanical properties, which differ from the properties of the individual components. Notwithstanding this, although the term "cocrystal" is generally understood in the art, there is no current agreed definition of that term, as is exemplified in a paper entitled "Polymorphs, Salts, and Cocrystals: What's in a Name?", Cryst. Growth Des., 2012, 12, 2147-2152, which was prompted by draft guidance issued by the United States Food and Drug Administration (FDA) relating to the definition of cocrystals for regulatory purposes. The authors of that paper considered the FDA guidance was too limited and proposed their own definitions of the term "cocrystal", the broadest version of which reads:

"cocrystals are solids that are crystalline single phase materials composed of two or more different molecular and/or ionic compounds generally in a stoichiometric ratio".

The multicomponent nature of cocrystals has previously been recognised as evidenced by paper entitled "The Salt-Cocrystal Continuum: The Influence of Crystal Structure on Ionisation State", Molecular Pharmaceuticals, Vol 4, No 3, 323-338. This paper notes that both salts and cocrystals are multicomponent and that, depending on a number of factors, in addition to salts and cocrystals a continuum containing both ionic crystalline species and cocrystalline species may exist.

Whatever definition of "cocrystal" may eventually be adopted, as used in this specification it is intended the term be interpreted broadly and not be artificially restricted by definitions such as that proposed by the FDA, which, as identified by the authors of the paper, are relatively restricted.

As mentioned above, cocrystals may be made in a variety of ways similarly to other crystalline forms of active materials, although such methods may not be without difficulties when applied to cocrystal manufacture. Methods of cocrystallisation include slow evaporation of a solvent from a solution containing cocrystal components; cocrystallising from a slurry of the components; cocrystallising from a melt; cocrystallising in a supercritical fluid; or wet or dry grinding of the components together. In the latter instance, the application of mechanical energy to the components appears to be a prerequisite in many methods. Examples of some of these methods may be found in EP 2170284, EP 2361247, US 2007/0287184, US 2009/0054455, US 2010/0204204, U.S. Pat. No. 7,927,613 and WO 2011/097372 and in "The role of mechanochemistry and supramolecular design in the development of pharmaceutical materials", CrystEngComm, 2012, 14, 2350-2362. More specifically, for example, US 2009/0054455 describes the synthesis of aripiprazole/fumaric acid cocrystals by dissolving aripiprazole and fumaric acid in a suitable solvent to form a clear solution of the components and then adding an anti-solvent to precipitate the cocrystals; and EP 2170284 describes using supercritical or liquefied gas to prepare a cocrystallisation medium containing a dissolved API and a dissolved co-former, cocrystals being recovered from the supercritical or liquefied gas by depressurisation.

The prior art methods for producing cocrystals are usually practised on a relatively small scale and scaling up such methods may present significant difficulties. For example, solvent-based methods would require substantial volumes of solvents resulting in lower yields of active crystalline materials. Mechanical or pressure methods would require relatively high capital investment.

There is a clear need for a simple, effective method of making active crystalline materials and, in particular, of making active multicomponent crystalline materials, and, especially, active cocrystalline materials.

SUMMARY OF THE INVENTION

The present invention provides a method of making active crystallinematerials. More particularly, the present invention provides a method of making active multicomponent crystalline materials, especially active cocrystalline materials.

The method of the invention involves dispersing precursor components of the active crystalline material in a liquid medium which comprises an anti-solvent, maintaining the dispersion for a period during which the active crystalline material is formed, and, during said period, exposing the dispersion to a solvent, which solvent being present in the liquid medium in a minor proportion by weight thereof.

More particularly, according to one embodiment of the present invention, a method for making an active crystalline material comprises dispersing precursor components of the active crystalline material in a liquid reaction medium which comprises an anti-solvent, maintaining the dispersion for a period during which the active crystalline material is formed, and, during said period, exposing the dispersion to a solvent, which solvent being present in the liquid medium in a minor proportion by weight thereof, wherein the anti-solvent is less capable of forming intermolecular interactions than the solvent, and wherein the active crystalline material is less soluble in the solvent than at least one of the precursor components.

In particular, depending upon the precursor components and the active crystalline material selected, the anti-solvent may be less capable of forming intermolecular interactions with the precursor components and the active crystalline material than the solvent. Further, while the anti-solvent may contribute to intermolecular interactions in an intermediate phase, i.e. as the reaction progresses, it is preferable that the anti-solvent is not capable of forming intermolecular interactions with the final product, i.e. the active crystalline material together with any unreacted precursor components.

More particularly, according to another embodiment of the present invention, a method for making an active multicomponent crystalline material, especially an active cocrystalline material, comprises dispersing precursor components of the active multicomponent crystalline material in a liquid reaction medium which comprises an anti-solvent, maintaining the dispersion for a period during which the active multicomponent crystalline material is formed, and, during said period, exposing the dispersion to a solvent, which solvent being present in the liquid medium in a minor proportion by weight thereof, wherein the anti-solvent is less capable of forming intermolecular interactions than the solvent, and wherein the active multicomponent crystalline material is less soluble in the solvent than at least one of the precursor components.

The term "anti-solvent" is used herein to mean an organic liquid in which at least one of the precursor components and the active crystalline material are essentially insoluble. This may be expressed as the solubility of at least one of the precursor components and the active crystalline material in the anti-solvent is preferably not more than 1 mg/g at 25° C. More preferably, the solubility of at least one of the precursor components and the active crystalline material in the anti-solvent is not more than 0.1 mg/g at 25° C. If one of the precursor components has any solubility in the anti-solvent, then preferably it has only limited solubility in the anti-solvent. In particular, if one of the precursor components has any solubility in the anti-solvent, then preferably the solubility of it in the anti-solvent is not more than 10 mg/g at 25° C. and, more especially is not more than 5 mg/g at 25° C. In preferred embodiments of the invention, all of the precursor components are essentially insoluble in the anti-solvent.

The term "solvent" is used herein to mean an organic liquid or water in which at least one and, preferably, all of the precursor components are soluble at least to some extent. This may be expressed as the solubility of the precursor components in the solvent is preferably at least 1 mg/g at 25° C. More preferably, the solubility of the precursor components in the solvent is at least 5 mg/g at 25° C. and, more especially, is at least 10 mg/g at 25° C.

Although the active crystalline material may have some solubility in the solvent, it is preferred that the precursor components have solubilities in the solvent that are greater than the solubility of the active crystalline material in the solvent. In particular, it is preferred that the precursor components have at least twice the solubility in the solvent than the solubility of the active crystalline material in the solvent. More especially, it is preferred that the precursor components have at least three times the solubility in the solvent than the solubility of the active crystalline material in the solvent.

In one embodiment of the invention, one of the precursor components has a solubility in the solvent that is greater than the solubility of the other or other precursor components present. Preferably, said one precursor component has a solubility in the solvent that is at least twice, more particularly at least three times, the solubility of the other or other precursor components present.

The period for which the dispersion is maintained, during which the active crystalline material is formed, may typically be from 5 minutes to 3 hours. However, it will be appreciated that this period is not absolute and so the dispersion may be maintained for a period until it is observed that the active crystalline material has formed via partial or full reaction of the precursor components.

In an embodiment of the invention, the liquid medium in which the precursor components are dispersed consists essentially of anti-solvent, the method comprising adding the solvent to the dispersion. In this embodiment, it may be preferable to maintain the dispersion for a prolonged period during which the active crystalline material is formed, for example, from 30 minutes to 3 hours. This may be done to ensure that the solvent is well dispersed in the liquid mixture and so enables the reaction to reach completion.

In an alternative embodiment of the invention, the liquid medium in which the precursor components are dispersed comprises a mixture of both anti-solvent and solvent. As the solvent is premixed into the liquid medium comprising the anti-solvent, it may be well dispersed prior to dispersion of the precursor components. Accordingly, in this embodiment, the reaction of the precursor components to form the active crystalline material may reach completion more quickly.

Preferably, the solvent is capable of forming intermolecular interactions by hydrogen (H) bonding. More, preferably, the solvent has H acceptor and/or donor sites to enable it to form H bonds.

Preferably, the precursor components have H acceptor and/or donor sites to enable hydrogen bonding between precursor components. Further, one or more of the precursor components may be capable of forming hydrogen bonds with H acceptor and/or donor sites of the solvent.

Preferably, the precursor components are solid and are added directly to the liquid reaction medium in their solid form. In other words, the precursor components do not need to be pre-dissolved or slurried with the anti-solvent and/or solvent. Preferably, the precursor components are in finely divided form. More particularly, the precursor components may be in the micron or sub-micron size ranges.

Preferably, the method comprises selecting precursor components that will form active multicomponent crystalline materials, more especially active cocrystalline materials.

Preferably, the method comprises selecting precursor components that will form active crystalline materials, said precursor components comprising active precursor components either alone or in combination with inactive precursor components. For example, active crystalline materials may be formed from at least two active precursor components or may be formed from at least one active precursor component and at least one inactive precursor component.

The selection of precursor components to form active crystalline materials are well-known, as described above. Accordingly, it would be readily apparent which precursor components are required to obtain a specific active crystalline material. The present invention relates to a new method of forming such active crystalline materials.

Preferably, each precursor component has at least one functional group selected from the group comprising ether, thioether, alcohol, thiol, aldehyde, ketone, thioketone, nitrate ester, phosphate ester, thiophosphate ester, ester, thioester, sulphate ester, carboxylic acid, phosphonic acid, phosphinic acid, sulphonic acid, amide, primary amine, secondary amine, tertiary amine, sp2 amine, thiocyanate, cyanamide, oxime, nitrile, diazo, organohalide, nitro, S-heterocyclic ring, thiophene, N-heterocyclic ring, pyrrole, O-heterocyclic ring, furan, epoxide, peroxide, hydroxamic acid, imidazole, and pyridine.

Ratios of precursor components vary depending on the particular components. For example, for an active cocrystalline material, ratios of an active pharmaceutical precursor component to a cocrystal coformer precursor component may be 1:1, 2:1, 1:2, 1.5:1 or 1:1.5.

Preferably, the method of the invention comprises dispersing the precursor components in the liquid medium and maintaining the dispersion using high mixing conditions.

High mixing may be achieved by subjecting the liquid medium to flow conditions in which a Reynolds Number of at least 100, more preferably greater than 500, and more especially greater than 2000 exists. Preferably, the high mixing may be achieved by subjecting the liquid medium to flow conditions in which a Reynolds Number of not more than 20000 exists.

The method may be performed in any suitable apparatus, which may be operated on a batch basis or on a continuous flow basis. Typical examples of suitable apparatus are: stirred vessels using any of a variety of agitator designs such as paddle, anchor, pitched-blade propeller; in-line rotor/stator mixers; and flow reactors of various designs including oscillatory baffle reactors, meso-reactors.

Preferably, when the method is performed in a non-pressurised apparatus, it may be performed at or near to ambient temperatures, for example typically in the range 0° C. to, or more practically just below, the boiling point of the liquid medium. In particular, the method may be performed at around ambient temperature. As will be appreciated, ambient temperature may vary from location to location and, consequently, the method may be conveniently performed for example within the temperature range 5° C. to 45° C., more preferably in the temperature range 15° C. to 35° C., and more especially in the temperature range 15° C. to 30° C., the upper limits of the ranges depending upon the boiling points of the anti-solvent and solvent in the liquid medium.

Preferably, the method may be performed at atmospheric pressure. As will be appreciated, atmospheric pressure may vary from location to location by small amounts, standard atmospheric pressure being defined as ~100 kPa. Consequently, the method may be performed at standard atmospheric pressure±10 kPa, more preferably at standard atmospheric pressure±5 kPa.

Alternatively, in a closed pressure system, the method may be performed at a pressure of between 0.5 kPa to 1000 kPa, more preferably 10 kPa to 600 kPa.

Preferably, the methods of the invention further comprise isolating the active crystalline material. The active crystalline material is a solid and can be isolated by any known techniques such as filtration by gravity or by suction, decantation, centrifugation and the like. The isolated active crystalline material can then be further dried to remove any residual solvent or anti-solvent.

Preferably, in the method of the invention, the anti-solvent comprises a major proportion of the liquid medium and the solvent comprises a minor proportion of the liquid medium. More particularly, the solvent comprises not more than 20% by wt, more especially not more than 10% by wt of the liquid medium. In a particularly preferred embodiment of the method of the invention, the solvent comprises not more than 5% by wt of the liquid medium.

Preferably, in the method of the invention, the solvent comprises at least 0.1% by wt, more especially at least 0.5% by wt of the liquid reaction medium. In a particularly preferred embodiment of the method of the invention, the solvent comprises at least 1% by wt of the liquid reaction medium.

Preferably, the anti-solvent comprises at least 50% by wt, more preferably at least 75% by wt, especially at least 90% by wt of the liquid medium. In certain embodiments of the present invention, the anti-solvent may comprise from 95% by wt to 99% by wt of the liquid medium.

Preferably, in the method of the invention, the liquid medium consists essentially of anti-solvent and solvent.

Preferably, the anti-solvent is a non-polar liquid organic compound that meets the solubility requirements for the anti-solvent as described above. In particular, the anti-solvent is selected on the basis that at least one of the precursor components and the active crystalline material are insoluble in this compound. The solubility of selected precursor components and active crystalline material in various compounds are readily appreciated.

The anti-solvent may be selected from the group comprising acyclic and cyclic aliphatic hydrocarbons and aromatic and at least partially hydrogenated dicyclic aromatic hydrocarbons, and mixtures thereof.

Preferably, the acyclic aliphatic hydrocarbons from which the anti-solvent may be selected comprise $C_5$ to $C_{16}$ alkanes, more preferably $C_5$ to $C_8$ alkanes, and especially $C_5$ to $C_7$ alkanes, and mixtures thereof.

Preferably, the cyclic aliphatic hydrocarbons from which the anti-solvent may be selected comprise $C_5$ to $C_{10}$ cycloalkanes, more preferably $C_5$ to $C_8$ cycloalkanes, and especially $C_5$ to $C_7$ cycloalkanes, and mixtures thereof.

Preferably, the aromatic hydrocarbons from which the anti-solvent may be selected comprise aromatic hydrocarbons of formula Ar—$(R)_n$ wherein Ar is a benzene ring residue or, each R is independently H or a $C_1$ to $C_5$ alkane chain and n is an integer from 1 to 3, more preferably aromatic hydrocarbons of formula Ar—$(R)_n$ wherein Ar is a benzene ring residue, each R is independently H or a $C_1$ to $C_3$ alkane chain and n is an integer from 1 to 3, and especially aromatic hydrocarbons of formula Ar—$(R)_n$ wherein Ar is a benzene ring residue, each R is independently H or a $C_1$ alkane chain and n is an integer from 1 to 3, and mixtures thereof.

The at least partially hydrogenated dicyclic aromatic hydrocarbons may be solvents such as 1,2-dihydronapthalene, 1,2,3,4-tetrahydronapthalene and decahydronapthalene.

In one embodiment of the present invention, the anti-solvent may be cyclohexane.

Preferably, the solvent is a polar aprotic or a polar protic liquid organic compound or water that meets the solubility requirements for the solvent as described above. It will be well-known which solvents meet the solubility requirements, in view of the precursor components and active crystalline material selected.

The polar aprotic solvent may be selected from the group comprising functional derivatives of carboxylic acids, carbonates, aldehydes, ketones, ethers, heterocyclic compounds, nitriles, sulphoxides, esters and amines and mixtures thereof.

Preferably, the functional derivatives of carboxylic acids the polar aprotic solvent may be selected from comprise amides or esters, more preferably amides or esters derived from $C_1$ to $C_{12}$ carboxylic acids, and especially amides or esters derived from $C_2$ to $C_8$ carboxylic acids, and mixtures thereof.

Preferably, the carbonates are dimethyl carbonate or diethyl carbonate or mixtures thereof.

Preferably, the aldehydes and ketones the polar aprotic solvent may be selected from comprise $C_1$ to $C_8$ aldehydes and $C_2$ to $C_9$ ketones, more preferably $C_1$ to $C_5$ aldehydes and $C_2$ to $C_6$ ketones, more especially $C_2$ to $C_4$ ketones, and mixtures thereof.

Preferably, the ethers from which the solvent may be selected comprise diethyl ether, 1,4-dioxane and tetrahydrofuran and mixtures thereof.

Preferably, the heterocyclic compounds the polar aprotic solvent may be selected from comprise $C_4$ to $C_7$ heterocyclic compounds containing one or two hetero atoms selected from oxygen, nitrogen and sulphur, more preferably $C_5$ or $C_6$ heterocyclic compounds containing one hetero atoms selected from oxygen, nitrogen and sulphur or mixtures thereof, more preferably from oxygen and nitrogen or mixtures thereof, more especially $C_5$ or $C_6$ heterocyclic compounds containing one oxygen atom, and mixtures thereof.

Preferably, the nitriles the polar aprotic solvent may be selected from comprise $C_2$ to $C_4$ nitriles, and especially $C_2$ or $C_3$ nitriles, and mixtures thereof.

Preferably, the sulphoxides the polar aprotic solvent may be selected from comprise $C_2$ to $C_6$ sulphoxides, and especially $C_2$ to $C_4$ sulphoxides, and mixtures thereof.

The polar protic solvent may be selected from the group comprising water, carboxylic acids, aliphatic alcohols, phenyl alcohols, esters and amines and mixtures thereof.

Preferably, the carboxylic acids the polar protic solvent may be selected from comprise $C_1$ to $C_{12}$ carboxylic acids, more preferably $C_1$ to $C_8$ carboxylic acids, and especially $C_2$ to $C_5$ carboxylic acids, and mixtures thereof.

Preferably, the aliphatic alcohols the polar protic solvent may be selected from comprise $C_1$ to $C_{12}$ aliphatic alcohols, more preferably $C_1$ to $C_8$ aliphatic alcohols, and especially $C_2$ to $C_5$ aliphatic alcohols, and mixtures thereof.

Preferably, the phenyl alcohols the polar protic solvent may be selected from comprise phenyl alcohols of formula Ph-R wherein Ph is phenyl and R is $(CH_2)_mOH$ where m is an integer from 1 to 3, and more preferably phenyl alcohols of formula Ph-R wherein Ph is phenyl and R is $(CH_2)_mOH$ where m is an integer 1 or 2, and mixtures thereof.

In a one embodiment of the invention, the solvent may be a polar protic solvent, more preferably methanol or ethanol, and especially methanol.

BRIEF DESCRIPTION OF THE DRAWINGS

The present invention will now be further described by way of illustration only with reference to the following Examples and by reference to the accompanying drawing, in which.

DETAILED DESCRIPTION OF THE PREFERRED EMBODIMENTS

As previously described, the present invention provides a method of making active crystalline materials and, in particular, a method of making active multicomponent crystalline materials, especially active cocrystalline materials. The Examples illustrate the method of the invention with reference to making active cocrystalline materials.

The method of the invention involves dispersing precursor components of the active crystalline material in a liquid medium which comprises an anti-solvent, maintaining the dispersion for a period during which the active crystalline material is formed, and, during said period, exposing the dispersion to a solvent, which solvent being present in the liquid medium in a minor proportion by weight thereof. In the preferred embodiment of the invention, the anti-solvent is less capable of forming intermolecular interactions than the solvent, and wherein the active crystalline material is less soluble in the solvent than the precursor components.

Figure 1:
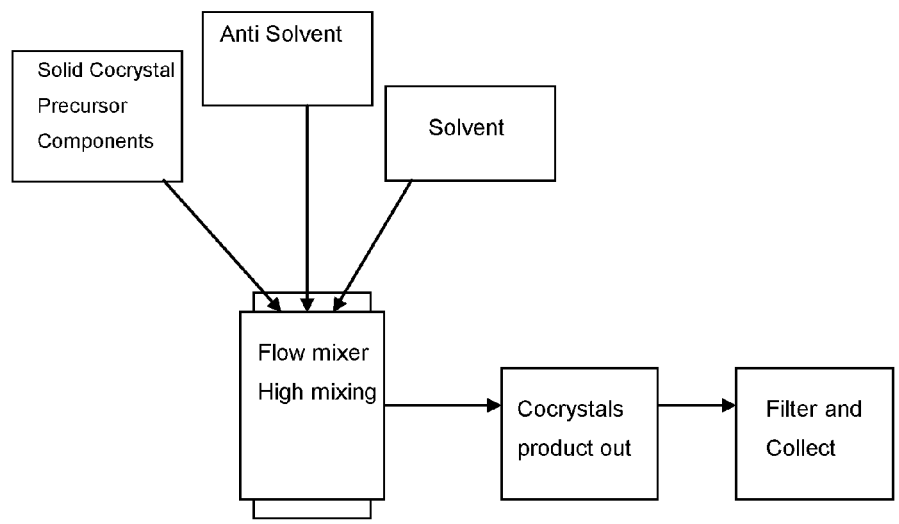
FIG. 1 is a flow diagram illustrating the method of the invention.

In one embodiment of the present invention, as indicated in FIG. 1, anti-solvent and solvent is introduced into for example a mixer to create a liquid medium, which is subjected to high mixing conditions. Solid particulate precursor components for the active crystalline material are then introduced into the mixer to disperse in the liquid medium. The mixer is operated for a period sufficient for the active crystalline material to form, following which the liquid medium is discharged from the mixer to permit separation of the active crystalline material and any residual precursor components from the liquid medium. The active cocrystalline material may then be further purified and/or dried by known techniques to produce a final product.

EXAMPLES

Example 1—Cocrystallisation of Caffeine and Oxalic Acid

Figure 2:
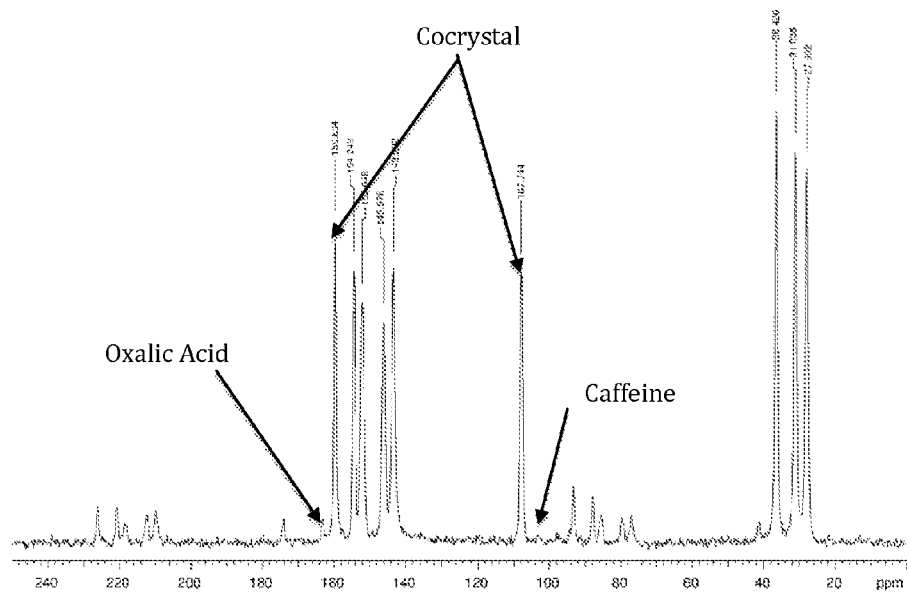
FIG. 2 is the solid state NMR spectrum for a caffeine: oxalic acid cocrystal.

An anti-solvent (33.4 g/97.8 wt % of anhydrous cyclohexane) and a solvent (0.75 g/2.2 wt % of anhydrous methanol) were poured into the mixer (an oscillatory baffle reactor) to form a liquid medium for cocrystallisation of the precursor components of the active cocrystalline material. The motion generator was operated to provide an oscillatory motion to the liquid medium (stroke amplitude=12.5 mm; frequency 1.5 Hz) and an active precursor component and a cocrystal coformer precursor component (2.05 g caffeine and 0.51 g oxalic acid (stoichiometric ratio 2:1), respectively) were then introduced into the mixer. The reaction took place at ambient temperature and pressure, which were not specifically measured during the reaction but for the laboratory concerned were typically in the ranges 17-22° C. and 96.6-104.28 kPa. After 30 minutes, the motion generator was stopped and the slurry of the liquid medium, active cocrystalline material and residual precursor components were removed from the flow mixer and were subjected to a filtration process. Any remaining solvent was allowed to evaporate from the residue. The residue (2.4 g) was analysed using solid state NMR (see FIG. 2) and confirmed to contain 1:2 caffeine:oxalic acid cocrystal (yield cocrystal=98.3%, caffeine=0% and oxalic acid=1.72%).

Example 2—Cocrystallisation of Carbamazepine and Nicotinamide

An anti-solvent (33.4 g/97.5 wt % of anhydrous cyclohexane) and a solvent (0.75 g/2.5 wt % of anhydrous methanol) were poured into the flow mixer to form a liquid medium for cocrystallisation of the precursor components of the active cocrystalline material. The motion generator was operated to provide an oscillatory motion to the liquid medium (stroke amplitude=10 mm; frequency 1.5 Hz) and an active precursor component and a cocrystal coformer precursor component (8.31 g carbamazepine and 4.3 g nicotinamide (stoichiometric ratio 1:1), respectively) were then introduced into the flow mixer. The reaction took place at ambient temperature and pressure as described in Example 1. After 3 hours, the motion generator was stopped and the slurry of the liquid medium, active cocrystalline material and residual precursor components were removed from the flow mixer and were subjected to a filtration process. Any remaining solvent was allowed to evaporate from the residue. The residue (11.1 g) was analysed using powder x-ray diffraction spectroscopy and confirmed to contain 1:1 carbamazepine:niotinamide cocrystal.

Example 3—Cocrystallisation of Caffeine and Oxalic Acid

An anti-solvent (33.4 g/96.1 wt % of hexane) and a solvent (1.34 g/3.9 wt % of anhydrous methanol) were poured into the mixer (round bottom flask provided with a PTFE paddle stirrer with over-head motor (at 180 rev/min)) to form a liquid medium for cocrystallisation of the precursor components of the active cocrystalline material. The paddle mixer was operated to stir the liquid medium and an active precursor component and a cocrystal coformer precursor component (2.05 g caffeine and 0.51 g oxalic acid (stoichiometric ratio 2:1, respectively) were then introduced into the mixer. The reaction took place at ambient temperature and pressure as described in Example 1. After 30 minutes, the paddle stirrer was stopped and the slurry of the liquid medium, active cocrystalline material and residual precursor components were removed from the round bottom flask and were subjected to a filtration process. Any remaining solvent was allowed to evaporate from the residue. The residue (2.5 g) was analysed using solid state NMR and confirmed to contain 1:2 caffeine:oxalic acid cocrystal (cocrystal=81.8% yield, caffeine=15.8% and oxalic acid=2.4%).

Example 4—Formation of 2-Aminopyrimidine and Salicylic acid salt

Figure 3:
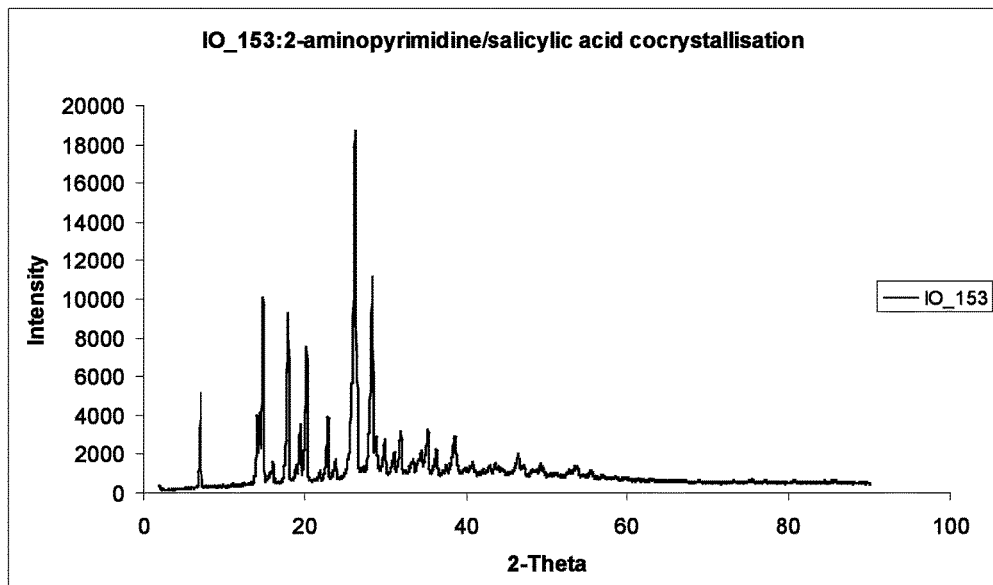
FIG. 3 is powder x-ray analysis of laboratory sample of salicylic:2-aminopyrimidine 1:1 salt
Figure 4:
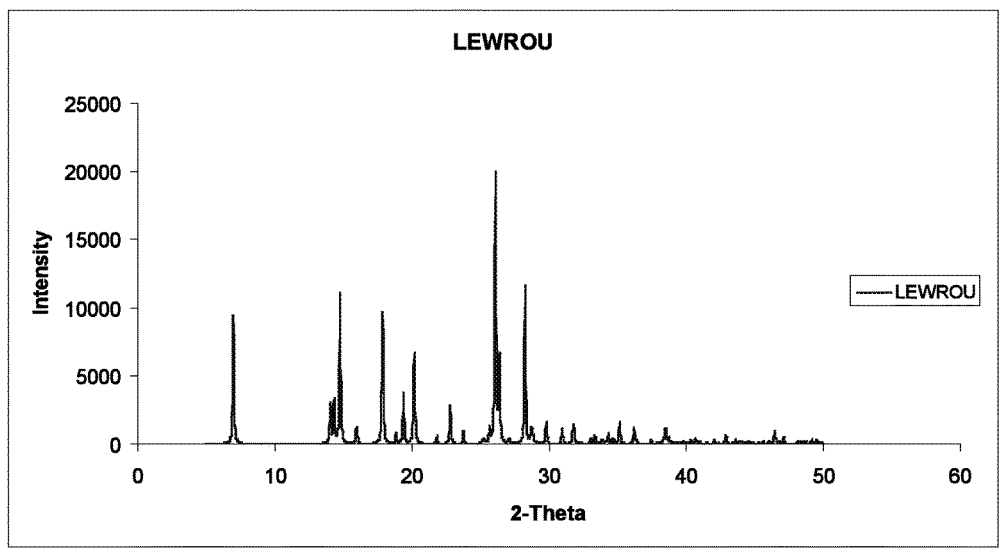
FIG. 4 is powder x-ray spectrum of 1:1 salicylic acid: 2-aminopyrimidine from Cambridge structural database.
Figure 5:
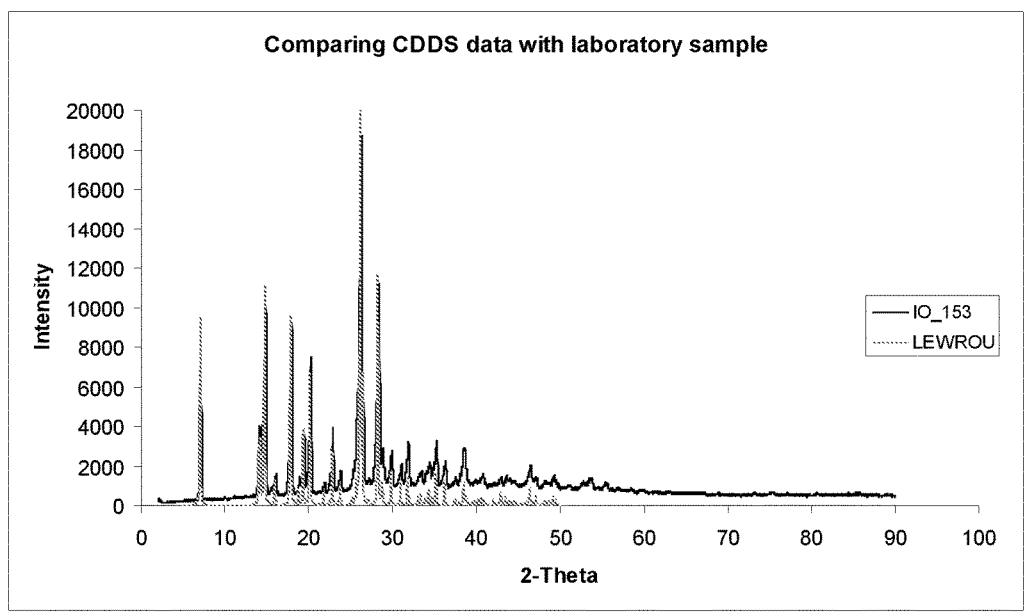
FIG. 5 is comparison of powder x-ray spectra of laboratory sample and Cambridge structure database.

An anti-solvent (33.4 g/97.8 wt % of anhydrous cyclohexane) and a solvent (0.75 g/2.2 wt % of anhydrous methanol) were poured into the mixer (an oscillatory baffle reactor) to form a liquid medium for salt formation of the precursor components. The motion generator was operated to provide an oscillatory motion to the liquid medium (stroke amplitude=12.5 mm; frequency 1.5 Hz) and the salt precursor components 1.38 g of salicylic acid and 0.95 g 2-aminopyrimidine (stoichiometric ratio 1:1 respectively) were then introduced into the mixer. The reaction took place at 16° C. but the pressure was not specifically measured during the reaction but for the laboratory concerned was typically between 96.6-104.28 kPa. After 30 minutes, the motion generator was stopped and the slurry of the liquid medium, the salt and residual precursor components were removed from the flow mixer and were subjected to a filtration process. Any remaining solvent was allowed to evaporate from the residue. The residue (2.11 g) was analysed using powder x-ray diffractometer (see FIG. 3) and confirmed to contain 1:1 2-aminopyrimidine:salicyclic acid salt by comparing the FIG. 3 spectrum with the spectrum of the salt (entry name LEWROU) on the Cambridge structure database, which is shown in FIG. 4, the comparison of the two spectra being shown in FIG. 5.

Example 5—Cocrystallisation of Caffeine and Oxalic Acid

An anti-solvent (33.4 g/96.1 wt % of hexane) and a solvent (1.34 g/3.9 wt % of anhydrous methanol) were weighed out separately. Half the hexane was poured into the mixer (round bottom flask provided with a PTFE paddle stirrer with over-head motor (at 180 rev/min)). The paddle mixer was operated to stir the liquid medium and an active precursor component and a cocrystal coformer precursor component (2.05 g caffeine and 0.51 g oxalic acid (stoichiometric ratio 2:1, respectively)) were then introduced into the mixer. The remaining hexane was added to help wash solids on the side of the flask into the liquid medium. After stirring for a minute the methanol was added to the reaction. The reaction took place at ambient temperature and pressure as described in Example 1. After 30 minutes, the paddle stirrer was stopped and the slurry of the liquid medium, active cocrystalline material and residual precursor components were removed from the round bottom flask and were subjected to a filtration process. Any remaining solvent was allowed to evaporate from the residue. The residue (2.56 g) was analysed using a powder x-ray diffractometer and confirmed to contain 1:2 caffeine:oxalic acid cocrystal.

The above was also repeated with anhydrous cyclohexane as the anti-solvent (33.4 g/97.8 wt %) and anhydrous methanol as the solvent (0.75 g/2.2 wt %). Again, the residue was analysed using a powder x-ray diffractometer and confirmed to contain 1:2 caffeine:oxalic acid cocrystals.

The invention claimed is:

1. A method for making an active crystalline material, the method comprising:
dispersing precursor components of the active crystalline material in a liquid medium comprising an anti-solvent to generate a dispersion;
exposing the dispersion to a solvent, wherein the solvent is present in the dispersion in a minor proportion by weight thereof; and
maintaining the dispersion to form the active crystalline material; and
wherein the step of exposing takes place during the period during which the active crystalline material is formed.

2. The method according to claim 1, wherein the solvent comprises not more than 20% by weight of the liquid medium.

3. The method according to claim 1, wherein the anti-solvent is less capable of forming intermolecular interactions than the solvent, and the active crystalline material is less soluble in the solvent than at least one of the precursor components.

4. The method according to claim 1, wherein dispersing includes dispersing in a liquid medium substantially free of the solvent.

5. The method according to claim 1 wherein the active crystalline material is selected from the group consisting of an active multi-component crystalline material and an active cocrystalline material.

6. The method according to claim 1, wherein the precursor components comprise solids and are added directly into the liquid medium.

7. The method according to claim 1, wherein the step of maintaining the dispersion further comprises applying high mixing conditions.

8. The method according to claim 1, further comprising isolating the active crystalline material.

9. The method according to claim 1, wherein the anti-solvent comprises a non-polar liquid organic compound selected from the group comprising of acyclic, cyclic aliphatic hydrocarbons, aromatic hydrocarbons and mixtures thereof.

10. The method according to claim 1, wherein the solvent is selected from the group consisting of a polar aprotic compound, a polar protic liquid organic compound and water.

11. The method according to claim 1, wherein the solvent comprises a polar aprotic liquid organic compound selected from the group consisting of functional derivatives of carboxylic acids, carbonates, aldehydes, ketones, ethers, heterocyclic compounds, nitriles, sulphoxides, esters, amines and mixtures thereof.

12. The method according to claim 1, wherein the solvent comprises a polar protic liquid organic compound selected from the group consisting of water, carboxylic acids, aliphatic alcohols, phenyl alcohols and mixtures thereof.

13. A method for making an active crystalline material, the method comprising:
dispersing precursor components of the active crystalline material in a liquid medium comprising an anti-solvent to generate a dispersion; and
maintaining the dispersion to form the active crystalline material, wherein a first portion of a solvent is added while maintaining the dispersion, the first portion of solvent comprising a minor proportion by weight of the liquid medium.

14. The method according to claim 13, wherein dispersing the precursor components includes dispersing in a liquid medium substantially free of solvent.

15. A method for making an active crystalline material, the method comprising:
dispersing precursor components of the active crystalline material in a liquid medium comprising an anti-solvent and a solvent to generate a dispersion;
maintaining the dispersion for a period during which the active crystalline material is formed,
wherein the solvent is present in the dispersion in a minor proportion by weight thereof,
wherein the anti-solvent is less capable of forming intermolecular interactions than the solvent, and
wherein the active crystalline material is less soluble in the solvent than at least one of the precursor components.

16. The method according to claim 15, wherein the solvent comprises not more than 20% by weight of the liquid medium.

17. The method according to claim 15 wherein the active crystalline material is selected from the group consisting of an active multi-component crystalline material and an active cocrystalline material.

18. The method according to claim 15, wherein the precursor components comprise solids and are added directly into the liquid medium.

19. The method according to claim 15, wherein the step of maintaining the dispersion further comprises applying high mixing conditions.

20. The method according to claim 15, further comprising isolating the active crystalline material.

21. The method according to claim 15, wherein the anti-solvent comprises a nonpolar liquid organic compound selected from the group comprising of acyclic, cyclic aliphatic hydrocarbons, aromatic hydrocarbons and mixtures thereof.

22. The method according to claim 15, wherein the solvent is selected from the group consisting of a polar aprotic compound, a polar protic liquid organic compound and water.

23. The method according to claim 15, wherein the solvent comprises a polar aprotic liquid organic compound selected from the group consisting of functional derivatives of carboxylic acids, carbonates, aldehydes, ketones, ethers, heterocyclic compounds, nitriles, sulphoxides, esters, amines and mixtures thereof.

24. The method according to claim 15, wherein the solvent comprises a polar protic liquid organic compound selected from the group consisting of water, carboxylic acids, aliphatic alcohols, phenyl alcohols and mixtures thereof.

25. The method of claim 1, wherein the period for which the dispersion is maintained and the active crystalline material is formed is from about 5 minutes to about 3 hours.

26. The method of claim 13, wherein the period for which the dispersion is maintained and the active crystalline material is formed is from about 5 minutes to about 3 hours.

27. The method of claim 15, wherein the period for which the dispersion is maintained and the active crystalline material is formed is from about 5 minutes to about 3 hours.

\* \* \* \* \*